United States Patent [19]

Cormany

[11] 4,217,310

[45] Aug. 12, 1980

[54] STABILIZATION OF CYCLOHEXENE OXIDE

[75] Inventor: Charles L. Cormany, Wadsworth, Ohio

[73] Assignee: PPG Industries, Inc., Pittsburgh, Pa.

[21] Appl. No.: 934,774

[22] Filed: Aug. 18, 1978

[51] Int. Cl.$^2$ ............................................. C07C 17/40
[52] U.S. Cl. ........................... 260/652.5 R; 260/348.38
[58] Field of Search ..................... 260/652.5 R, 348.38

[56] References Cited

U.S. PATENT DOCUMENTS

| | | | |
|---|---|---|---|
| 3,120,567 | 2/1964 | Dial | 260/652.5 R |
| 3,265,747 | 8/1966 | Cormany et al. | 260/652.5 R |
| 3,549,715 | 12/1970 | Cormany et al. | 260/652.5 R |
| 3,627,834 | 12/1971 | Patron | 260/652.5 R |
| 3,714,052 | 1/1973 | Beckers | 260/652.5 R X |
| 3,746,648 | 7/1973 | Peoples | 260/652.5 R |

*Primary Examiner*—Helen M. S. Sneed
*Attorney, Agent, or Firm*—Edward J. Whitfield

[57] ABSTRACT

Cyclohexene oxide is stabilized against peroxidative decomposition by inclusion therein of a stabilizing amount of glycidol. The glycidol stabilized cyclohexene oxide is particularly suited in stabilizing unsaturated chlorinated solvents, e.g., perchloroethylene and trichloroethylene against metal induced decomposition.

6 Claims, No Drawings

STABILIZATION OF CYCLOHEXENE OXIDE

BACKGROUND OF THE INVENTION

Oxirane compounds such as epichlorohydrin, cyclohexene oxide, glycidol, glycidyl ethers, and the like, usually in combination with other compounds such as alkoxynitriles, amines, amides, alcohols, and esters, are commonly used to stabilize chlorinated solvents, such as perchloroethylene, against metal induced decomposition.

Of the oxirane compounds, epichlorohydrin is perhaps most commonly used due to its proven effectiveness and ready availability. However, since epichlorohydrin has been shown by the Ames Test to exhibit mutagenic activity, its continued permissible use in chlorinated solvent stabilization systems is questionable for reasons of health and safety.

Cyclohexene oxide has been demonstrated to be an acceptable non-mutagenic substitute for epichlorohydrin in chlorinated solvent stabilization systems; however, cyclohexene oxide suffers from the disadvantage that it, itself, is unstable and develops acidity upon storage, especially when exposed to air.

It is believed that cyclohexene oxide autoperoxidizes to form a decomposition product which is believed to be cyclopentane carboxylic acid, which decomposition product causes severe pitting and corrosion of metals, particularly aluminum. Consequently, before cyclohexene oxide can be effectively used to stabilize chlorinated solvents against metal induced decomposition, the cyclohexene oxide itself must be stabilized against peroxidative decomposition.

Cyclohexene oxide is usually stabilized against decomposition by the inclusion of a stabilizing amount of butylated hydroxytoluene (BHT). However, it has been found that BHT stabilized cyclohexene oxide is not very effective in stabilizing unsaturated chlorinated solvents, for example, perchloroethylene, against metal, particularly aluminum, induced decomposition, especially when the solvent is used in degreasing operations.

It is desirable, therefore, to devise means of stabilizing cyclohexene oxide against decomposition, which stabilized cyclohexene oxide would be particularly effective in stabilizing unsaturated chlorinated solvents against metal induced decomposition in addition to having the capacity to neutralize any hydrochloric acid decomposition product.

DESCRIPTION OF THE INVENTION

In accordance with this invention, it has been found that cyclohexene oxide is stabilized against peroxidative decomposition by the inclusion therein of a stabilizing amount of glycidol.

The quantity of glycidol used to stabilize cyclohexene oxide may vary over a wide range. Sufficient glycidol is used such that the cyclohexene oxide contains at least about 1.5 weight percent glycidol although the cyclohexene oxide may contain up to 25 weight percent or more of glycidol. Typically sufficient glycidol is used such that the cyclohexene oxide contains from about 3 weight percent to about 25 weight percent glycidol.

The glycidol stabilized cyclohexane oxide is particularly effective in stabilizing unsaturated chlorinated solvents such as perchloroethylene or trichloroethylene against metal, e.g., aluminum, induced decomposition. When used to stabilize chlorinated solvents, the glycidol stabilized cyclohexene oxide is employed in typical stabilizing amount, i.e., such that the solvent contains from about 0.01 percent to about 0.5 percent by weight usually from about 0.03 percent to about 0.3 percent by weight cyclohexene oxide, although the solvent may contain so much as 1.0 percent or more by weight of cyclohexene oxide.

The cyclohexene oxide may be stabilized with glycidol prior to stabilizing the solvent or unstabilized cyclohexene oxide and glycidol may be added separately to the solvent thus stabilizing the cyclohexene oxide in situ.

The stabilization afforded cyclohexene oxide by glycidol is not appreciably affected by the presence of stabilizing amounts of other commonly used chlorinated solvent stabilizing components such as, for example, phenols, alcohols, esters, amines, amides, nitriles, and the like.

The invention is further illustrated but is not intended to be limited by the following examples.

EXAMPLE 1

A series of stabilized perchloroethylene samples was prepared using the following stabilization systems. The stabilizing materials are expressed as percent by weight based on the weight of perchloroethylene:

| Sample No. | 1 | 2 | 3 |
|---|---|---|---|
| CHO | 0.27 | 0.27 | 0.27 |
| HQMME | 0.01 | 0.01 | 0.01 |
| NMM | 0.005 | 0.005 | 0.005 |
| EPN | 0.06 | 0.06 | 0.06 |
| GDL | — | 0.005(a) | 0.01(b) |

(a) 1.82 weight percent GDL based on weight of CHO plus GDL.
(b) 3.57 weight percent GDL based on weight of CHO plus GDL.

Legend:  CHO - cyclohexane oxide
HOMME - hydroquinone monomethyl ether
NMM - N-methylmorpholine
EPN - beta-ethoxypropionitrile
GDL - glycidol 100 milliliters of each of the above stabilized solvents were placed in individual 250 milliliter Erlenmeyer flasks. A 2024 aluminum coupon measuring ½ inch ×4 inches ×1/32 inch was placed in each flask. Each coupon was polished with a crocus cloth and cleaned with acetone immediately prior to its being placed in its respective flask. Each flask was provided with a reflux condenser and heated to refluxing temperature. The flask contents were refluxed until visible signs of corrosion, i.e., black spots, appeared on the coupons. Under the microscope, these spots appeared as small craters covered with a reddish-brown powder.

The results of the reflux tests are as follows:

| Sample | Days Until Corrosion Observed | Days Until Test Terminated |
|---|---|---|
| 1 | 5 | 5 |
| 2 | None | 35 |
| 3 | None | 37 |

EXAMPLE 2

A simulated glass degreaser was constructed from a three-liter capacity, one-neck round bottom flask, a two-liter capacity flask, and a water-cooled condenser.

The condenser outlet was connected by rubber tubing to a safety trap and a silver nitrate trap connected in series. The two-liter flask was modified by inserting and fusing a piece of glass tubing with a 24/40 T male joint through the bottom of the flask. One end of the tube extended about halfway into the flask such that about one liter of solvent could be collected before overflowing back into the bottom three-liter flask (simulated boiling sump). Before starting the test, about 60 grams each of 2024 and 7075 aluminum turnings, 200 milliliters of Limex 78 oil and two liters of perchloroethylene were added to the boiling sump. The modified two-liter flask (simulated rinse tank) was fitted to the three-liter flask and 500 milliliters of perchloroethylene were added to the two-liter flask. The assembly was heated to and maintained at reflux temperature by means of a Variac controlled heating mantle. Solvent decomposition was indicated by the appearance of a white silver chloride precipitate in the silver nitrate trap.

One test was run using perchloroethylene that was stabilized by the addition thereto of 0.27 weight percent cyclohexene oxide, 0.01 weight percent glycidol and 0.01 weight percent hydroquinone monomethyl ether (solvent A).

Another test was run using perchloroethylene stabilized as above except that no glycidol was added (solvent B).

Samples of perchloroethylene were taken from the boiling sump at periodic intervals and analyzed for acid acceptance. The results of these tests are summarized as follows:

| Days Reflux | Solvent A | | Solvent B | |
|---|---|---|---|---|
| | pH | Acid Acceptance, % | pH | Acid Acceptance, % |
| 0 | 8.23 | 0.106 | 8.21 | 0.099 |
| 4 | 7.95 | 0.095 | 8.00 | 0.092 |
| 7 | 7.90 | 0.096 | 7.90 | 0.091 |
| 11 | 8.00 | 0.095 | 7.75 | 0.081 |
| 18 | 7.75 | 0.094 | 7.80 | 0.051 |
| 25 | 7.70 | 0.094 | 7.75 | 0.016 |
| 32 | — | — | 5.10 | −0.038 |
| 66 | 8.07 | 0.069 | — | — |

As seen from the above, perchloroethylene stabilized with unstabilized cyclohexene oxide (solvent B) develops acidity more rapidly under simulated degreasing conditions than perchloroethylene stabilized with glycidol stabilized cyclohexene oxide (solvent A). Moreover, examination of the aluminum turnings showed no attack from solvent A whereas the aluminum turnings were severely pitted from solvent B.

The acid acceptance of the solvent is a measure of the capacity of the solvent to neutralize hydrochloric acid and is expressed in percent by weight of equivalent sodium hydroxide. The acid acceptance is determined as follows. To an Erlenmeyer flask is added 25 milliliters of 0.1 N hydrochloric acid in isopropyl alcohol, 10 milliliters of solvent, and 25 milliliters of isopropyl alcohol. The contents of the flask are thoroughly mixed, the flask is stoppered and allowed to stand for 10 minutes at room temperature. Three drops of bromophenol blue indicator are added and the flask contents are titrated with 0.1 N sodium hydroxide to the blue-green end point.

A blank determination is made by titrating 25 milliliters of 0.1 N hydrochloric acid in isopropyl alcohol and 25 milliliters of isopropyl alcohol with 0.1 N sodium hydroxide to the blue-green bromophenol blue end point.

Acid acceptance in weight percent equivalent sodium hydroxide is calculated as follows:

$$\text{Acid Acceptance} = \frac{(K - S)N \times 0.04 \times 100}{W}$$

wherein:
K=milliliters of NaOH solution required for the blank titration;
S=milliliters of NaOH solution required for the sample titration;
N=normality of the NaOH solution; and
W=grams of sample (volume in milliliters × specific gravity).

EXAMPLE 3

A first sample of perchloroethylene was stabilized by the addition thereto of 0.245 weight percent cyclohexene oxide, 0.025 weight percent glycidol, 0.01 weight percent hydroquinone monomethyl ether and 0.06 weight percent beta-ethoxypropionitrile and 0.005 weight percent N-methylmorpholine (solvent C).

A second sample of perchloroethylene was stabilized by the addition thereto of 0.27 weight percent cyclohexene oxide, 0.01 weight percent hydroquinone monomethyl ether, 0.06 weight percent betaethoxypropionitrile and 0.005 weight percent N-methylmorpholine (solvent D).

Solvent C and solvent D were each tested in a Baron-Blakeslee model MVW-125 vapor-spray degreaser.

After 838 hours of operation, a sample of solvent C taken from the boiling sump had a pH of 7.31 and an acid acceptance of 0.180 percent. No sign of corrosion was observed on a 2024 aluminum test panel that had been immersed in the solvent in the boiling sump throughout the test period.

After 574 hours of operation, a sample of solvent D taken from the boiling sump had a pH of 7.7 and an acid acceptance of 0.094 percent. A 2024 aluminum test panel that had been immersed in the boiling sump throughout the test period was severely corroded and pitted.

EXAMPLE 4

Clear glass bottles were filled to about two-thirds capacity with samples of neat cyclohexene oxide and cyclohexene oxide containing 10 weight percent glycidol. The bottles were stoppered and stored at room temperature. After 23 days storage, the relative peroxide contents of the samples were measured by determining the amount of 0.01 N sodium thiosulfate solution required to react with the iodine liberated when 25 milliliters of sample was treated with a sodium iodide/acetone solution. The neat cyclohexene oxide required 13.05 milliliters of 0.01 N sodium thiosulfate solution to react the liberated iodine whereas only 0.85 milliliters of 0.01 N sodium thiosulfate was required to react the liberated iodine in the glycidol containing cyclohexene oxide. After 58 days storage, the thiosulfate titers were 13.70 milliliters and 2.05 milliliters for the neat cyclohexene oxide and glycidol containing cyclohexene oxide, respectively.

Although the invention has been described with specific references and specific details of embodiments thereof, it is to be understood that it is not intended to be so limited since changes and alterations therein may be made by those skilled in the art which are within the full intended scope of this invention as defined by the appended claims.

I claim:

1. Cylclohexene oxide stabilized against peroxidative auto-decomposition by inclusion therein of at least about 1.5 percent by weight glycidol.

2. The composition of claim 1 wherein the cyclohexene oxide contains from about 3.0 percent to about 25 percent by weight glycidol.

3. An unsaturated chlorinated solvent stabilized against metal induced decomposition by inclusion therein of from about 0.01 percent to 1.0 percent by weight cyclohexene oxide and at least about 1.5 percent by weight glycidol based on the combined weight of cyclohexene oxide and glycidol.

4. The composition of claim 3 containing from about 3.0 percent to about 25 percent by weight glycidol based on the combined weight of cyclohexene oxide and glycidol.

5. The composition of claim 3 wherein the solvent is perchloroethylene.

6. The composition of claim 3 wherein the solvent contains from about 0.03 to 0.3 percent by weight cyclohexene oxide.

* * * * *